United States Patent
Ryu et al.

(10) Patent No.: US 8,034,489 B2
(45) Date of Patent: Oct. 11, 2011

(54) SILANE COMPOUND, ORGANIC ELECTROLYTE SOLUTION USING THE SILANE COMPOUND, AND LITHIUM BATTERY USING THE ORGANIC ELECTROLYTE SOLUTION

(75) Inventors: Young-gyoon Ryu, Yongin-si (KR); Sang-kook Mah, Yongin-si (KR); Jae-young Choi, Yongin-si (KR); Seok-soo Lee, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 1236 days.

(21) Appl. No.: 11/688,783

(22) Filed: Mar. 20, 2007

(65) Prior Publication Data

US 2008/0044735 A1 Feb. 21, 2008

(30) Foreign Application Priority Data

Aug. 16, 2006 (KR) .................. 10-2006-0077126

(51) Int. Cl.
*H01M 6/18* (2006.01)
(52) U.S. Cl. ........ 429/313; 429/316; 429/317; 429/330; 429/332; 429/326; 252/62.2

(58) Field of Classification Search .................. 429/313, 429/316, 317, 330, 332, 326; 252/62.2
See application file for complete search history.

(56) References Cited

FOREIGN PATENT DOCUMENTS

| JP | 58-216194 | 12/1983 |
| JP | 11-100571 | 4/1999 |
| JP | 2005-232445 | 9/2005 |
| JP | 2005-314246 | 11/2005 |

OTHER PUBLICATIONS

Megahed, et al, "Lithium-ion rechargeable batteries," Journal of Power Sources, 51 (1994) pp. 79-104.
Japanese Office action dated Jun. 8, 2010, for corresponding Japanese Patent application 2007-188669, noting listed references in this IDS.
Patent abstract of Japan for publication No. 2005-314246 dated Nov. 10, 2005 by Keiji Wakita.

*Primary Examiner* — Laura Weiner
(74) *Attorney, Agent, or Firm* — Christie, Parker & Hale, LLP

(57) ABSTRACT

Organic electrolyte solutions and lithium batteries using the same are provided. The organic electrolyte solutions use a silane compound that prevents crack formation caused by volumetric changes in the anode active material during battery charging/discharging. This improves charge/discharge characteristics, thereby also improving stability, reliability, and charge/discharge efficiency of the battery.

20 Claims, 4 Drawing Sheets

SILANE COMPOUND, ORGANIC ELECTROLYTE SOLUTION USING THE SILANE COMPOUND, AND LITHIUM BATTERY USING THE ORGANIC ELECTROLYTE SOLUTION

CROSS-REFERENCE TO RELATED PATENT APPLICATION

This application claims priority to and the benefit of Korean Patent Application No. 10-2006-0077126, filed on Aug. 16, 2006 in the Korean Intellectual Property Office, the entire content of which is incorporated herein by reference.

BACKGROUND OF THE INVENTION

1. Field of the Invention

The present invention relates to lithium batteries. More particularly, the invention relates to silane compounds, organic electrolyte solutions using the silane compounds, and lithium batteries using the organic electrolyte solutions.

2. Description of the Related Art

As portable electronic devices, such as video cameras, cellular phones, and notebook PCs, become lighter and have higher performance, much research into batteries as driving power sources for the devices has been conducted. In particular, re-chargeable (secondary) lithium batteries have been actively studied because they have energy densities (per unit weight) three times greater than those of conventional lead storage batteries, nickel-cadmium batteries, nickel hydrogen batteries, nickel zinc batteries, etc. In addition, lithium secondary batteries can be rapidly re-charged.

Conventional lithium batteries are operated at high operating voltages, and thus, conventional aqueous electrolyte solutions cannot be used due to the vigorous reaction of the aqueous solution with the lithium used as the anode. In this regard, organic electrolyte solutions obtained by dissolving lithium salts in organic solvents are generally used in lithium batteries. In particular, organic solvents having high ion conductivity, high dielectric constants, and low viscosities have been used. However, it is difficult to obtain a single organic solvent having all of these properties, and thus, mixed solvents have been proposed, for example an organic solvent including a solvent with a high dielectric constant and another organic solvent with low viscosity.

When a carbonate-based, non-aqueous polar solvent is used in a lithium secondary battery, excess charge occurs due to a reaction between the carbon of the anode and the electrolyte solution during initial charging. Such an irreversible reaction forms a passivation layer, such as a solid electrolyte interface (SEI) film, on the surface of the anode. The SEI film prevents further decomposition of the electrolyte solution and maintains stable charging/discharging. The SEI film also serves as an ion tunnel through which only lithium ions pass. In general, organic solvents solvate lithium ions, and are cointercalated with lithium ions into a carbon anode during battery charging/discharging. However, SEI films allow only lithium ions to pass, thereby preventing the cointercalation of organic solvents with lithium ions into the carbon anode. This prevents degradation of the anode structure caused by the cointercalation of solvents and lithium ions during battery charging/discharging.

However, the SEI film gradually cracks and delaminates from the surface of the electrode due to volumetric expansion and shrinkage of the active material during repeated charging/discharging. As a result, the electrolyte directly contacts the active material, causing continuous decomposition of the electrolyte. Once the SEI film cracks, the crack continuously extends during charging/discharging, thereby degrading the active material. In particular, when the active material contains a metal, such as silicon, active material degradation worsens due to large volumetric changes during charge/discharge cycles. Furthermore, repeated volumetric shrinkage and expansion of the active material causes agglomeration of silicon particles.

SUMMARY OF THE INVENTION

In one embodiment of the present invention, a new silane compound is provided.

In another embodiment of the present invention, an organic electrolyte solution uses the silane compound. In one embodiment, the electrolyte solution prevents direct contact between the metal active material and the electrolyte. According to another embodiment, the electrolyte solution prevents reductions in the conduction characteristics of the lithium ions.

In another embodiment, a lithium battery employs the organic electrolyte solution. According to one embodiment, the lithium battery has improved charge/discharge characteristics.

In one embodiment of the present invention, a silane compound comprises a compound represented by Formula 1 below.

Formula 1:

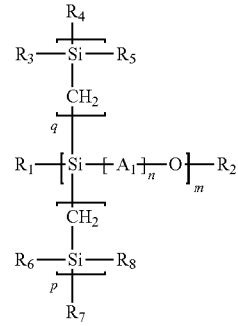

In Formula 1, n is a real number ranging from 1 to 20, m is an integer ranging from 1 to 10, and each of p and q is independently selected from 0 or 1. Each of $R_1$, $R_3$, $R_4$, $R_5$, $R_6$, $R_7$, and $R_8$ is independently selected from unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups. $R_2$ is selected from unsubstituted $C_{1-20}$ alkyl groups and halogen substituted $C_{1-20}$ alkyl groups. $A_1$ is a polar repeating unit selected from $C_{1-5}$ oxyalkylene groups, carbonyl groups,

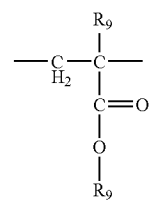

groups and mixtures thereof. In the $A_1$ repeating unit, $R_9$ is selected from hydrogen, unsubstituted $C_{1-20}$ alkyl groups and halogen substituted $C_{1-20}$ alkyl groups. At least one of $R_3$, $R_4$, $R_5$, $R_6$, $R_7$, and $R_8$ is selected from unsubstituted $C_{1-20}$ alkoxy groups and halogen substituted $C_{1-20}$ alkoxy groups.

According to one embodiment of the present invention, the silane compound of Formula 1 may be a compound represented by Formula 2 below.

Formula 2:

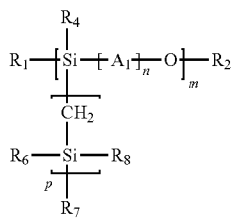

In Formula 2, $R_1$, $R_2$, $R_4$, $R_6$, $R_7$, $R_8$, n, m, and p are as defined above with respect to Formula 1.

According to another embodiment of the present invention, in the silane compound of Formula 1 above, $A_1$ may be selected from oxyethylene groups, oxypropylene groups, oxybutylene groups, oxypentylene groups, and the like.

According to yet another embodiment of the present invention, in the silane compound of Formula 1 above, at least one of $R_4$, $R_6$, $R_7$, and $R_8$ may be selected from methoxy groups, ethoxy groups, propoxy groups, butoxy groups, pentoxy groups, and the like.

According to still another embodiment of the present invention, the silane compound may be selected from compounds represented by Formulae 3 through 8 below, and combinations thereof.

Formula 3:

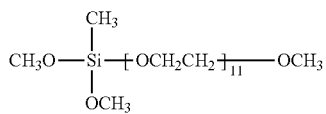

Formula 4:

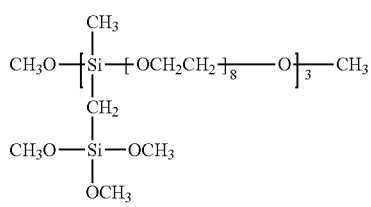

Formula 5:

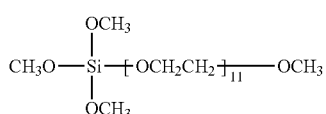

Formula 6:

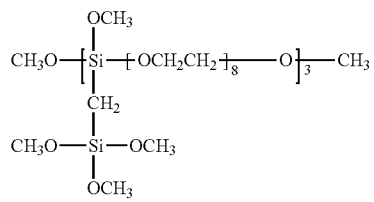

Formula 7:

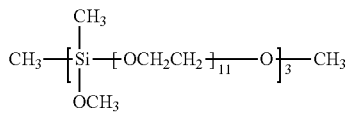

Formula 8:

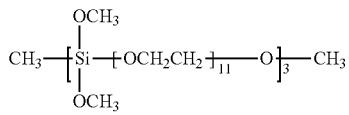

According to another embodiment of the present invention, an organic electrolyte solution includes a lithium salt, an organic solvent including a high dielectric constant solvent and a low boiling point solvent, and a silane compound represented by Formula 1 above.

According to another embodiment of the present invention, in the organic electrolyte solution, the silane compound may be a compound represented by Formula 2 above.

According to yet another embodiment of the present invention, in the organic electrolyte solution including the silane compound of Formula 1 or 2 above, $A_1$ may be selected from oxyethylene groups, oxypropylene groups, oxybutylene groups, oxypentylene groups, and the like.

According to still another embodiment of the present invention, in the organic electrolyte solution including the silane compound of Formula 1 or 2 above, at least one of $R_4$, $R_6$, $R_7$, and $R_8$ may be selected from methoxy groups, ethoxy groups, propoxy groups, butoxy groups, pentoxy groups, and the like.

According to still yet another embodiment of the present invention, in the organic electrolyte solution, the silane compound may be selected from compounds represented by Formulae 3 through 8 below and combinations thereof.

Formula 3:

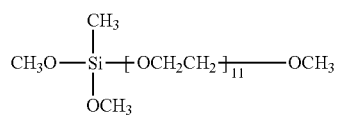

Formula 4:

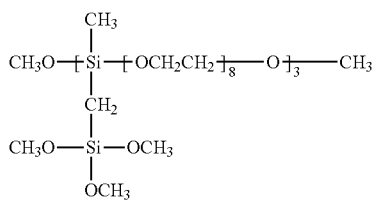

-continued

Formula 5:

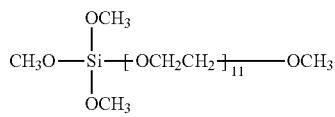

Formula 6:

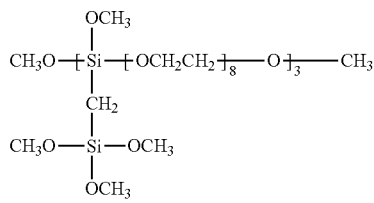

Formula 7:

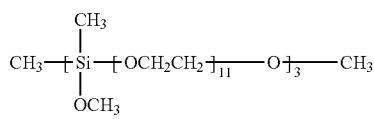

Formula 8:

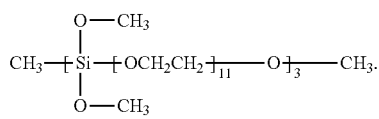

According to another embodiment of the present invention, in the organic electrolyte solution, the silane compound may be present in an amount ranging from about 0.5 to about 20 wt % based on the total weight of the organic solvent.

According to another embodiment of the present invention, in the organic electrolyte solution, the silane compound may be present in an amount ranging from about 1 to about 15 wt % based on the total weight of the organic solvent.

According to yet another embodiment of the present invention, in the organic electrolyte solution, the concentration of the lithium salt may range from about 0.5 to about 2.0M.

According to still another embodiment of the present invention, in the organic electrolyte solution, the high dielectric constant solvent may be selected from ethylene carbonate, propylene carbonate, butylene carbonate, gamma butyrolactone, and the like.

According to still yet another embodiment of the present invention, in the organic electrolyte solution, the low boiling point solvent may be selected from dimethyl carbonate, ethylmethyl carbonate, diethyl carbonate, dipropyl carbonate, dimethoxyethane, diethoxyethane, fatty acid ester derivatives, and the like.

According to yet another embodiment of the present invention, a lithium battery includes a cathode, an anode, and the organic electrolyte solution.

BRIEF DESCRIPTION OF THE DRAWINGS

The above and other features and advantages of the present invention will be better understood by reference to the following detailed description when considered in conjunction with the attached drawings in which.

DETAILED DESCRIPTION OF THE INVENTION

Figure 1:
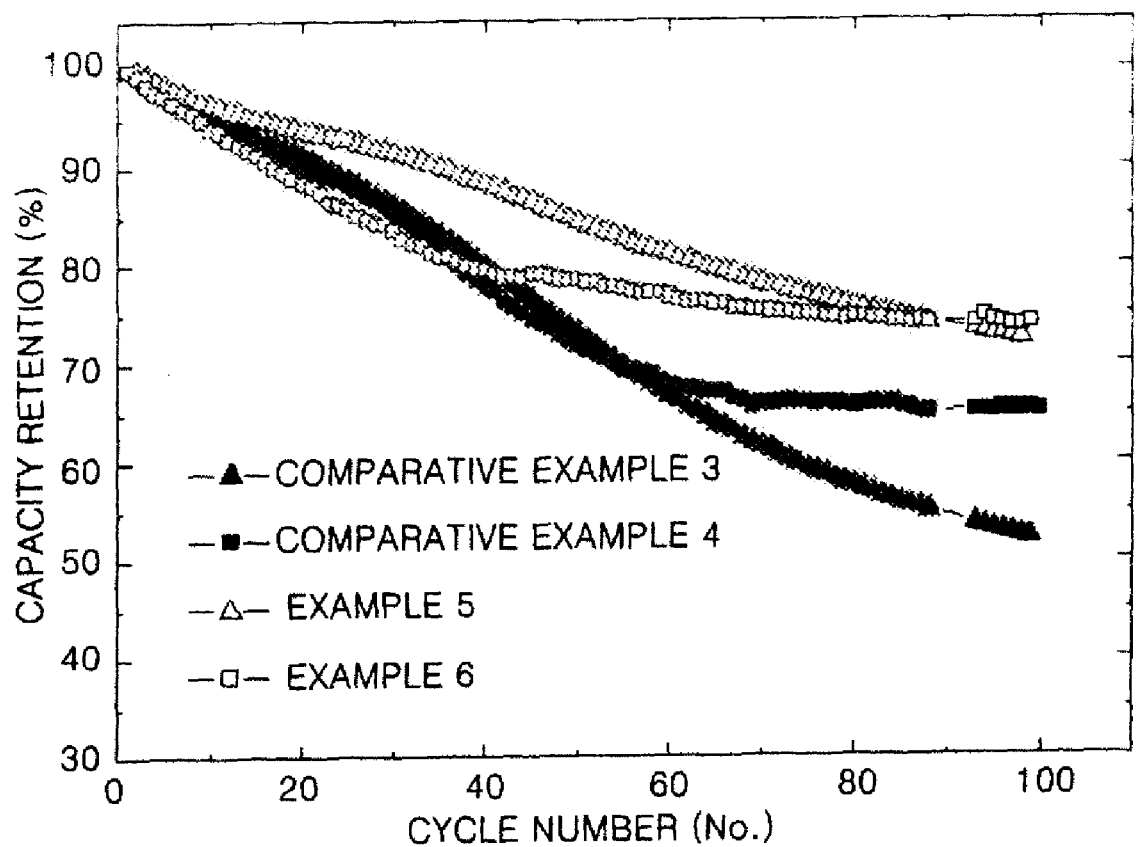
FIG. 1 is a graph of the charge/discharge efficiencies of the lithium batteries prepared according to Examples 5 and 6 and Comparative Examples 3 and 4.

The present invention will now be described with reference to the accompanying drawings, which illustrate some exemplary embodiments of the invention.

In one embodiment, the present invention provides a silane compound. In another embodiment, an organic electrolyte solution includes the silane compound. In yet another embodiment, a lithium battery uses the organic electrolyte solution. In one embodiment, the organic electrolyte solution including the silane compound prevents crack formation, which may be caused by volumetric changes in the anode active material during battery charging/discharging. Such prevention of crack formation improves charge/discharge characteristics, which in turn improves the stability, reliability, and charge/discharge efficiency of the battery.

A silane compound according to one embodiment of the present invention includes an end having an alkoxy group directly connected to a silicon atom, and another end including a polar repeating unit connected to the silicon atom. In one embodiment, for example, the silane compound includes compounds represented by Formula 1 below.

Formula 1:

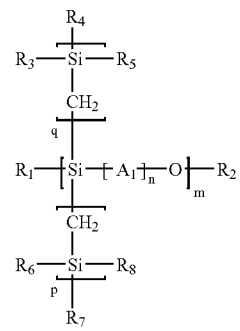

In Formula 1, n is a real number ranging from 1 to 20, m is an integer ranging from 1 to 10, and each of p and q is independently selected from 0 or 1. Each of $R_1$, $R_3$, $R_4$, $R_5$, $R_6$, $R_7$, and $R_8$ is independently selected from unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups. $R_2$ is selected from unsubstituted $C_{1-20}$ alkyl groups and halogen substituted $C_{1-20}$ alkyl groups. $A_1$ is a polar repeating unit selected from $C_{1-5}$ oxyalkylene groups, carbonyl groups,

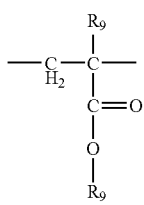

groups and mixtures thereof. In the $A_1$ repeating unit, $R_9$ is selected from hydrogen, unsubstituted $C_{1-20}$ alkyl groups and halogen substituted $C_{1-20}$ alkyl groups. At least one of $R_3$, $R_4$, $R_5$, $R_6$, $R_7$, and $R_8$ is selected from unsubstituted $C_{1-20}$ alkoxy groups and halogen substituted $C_{1-20}$ alkoxy groups.

In another embodiment, the silane compound of Formula 1 above is a compound represented by Formula 2 below.

Formula 2:

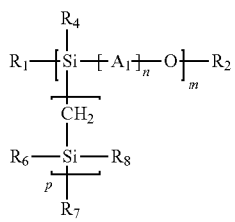

In Formula 2, $R_1$, $R_2$, $R_4$, $R_6$, $R_7$, $R_8$, n, m, and p are as defined above with respect to Formula 1.

According to one embodiment, in the silane compound of Formula 1 or 2 above, $A_1$ may be selected from oxyethylene groups, oxypropylene groups, oxybutylene groups, oxypentylene groups, and the like. In another embodiment, at least one of $R_4$, $R_6$, $R_7$, and $R_8$ may be selected from methoxy groups, ethoxy groups, propoxy groups, butoxy groups, pentoxy groups, and the like.

According to yet another embodiment, the silane compound is selected from compounds represented by Formulae 3 through 8 below and combinations thereof.

Formula 3:

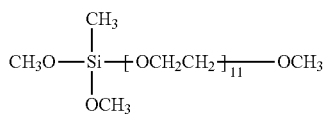

Formula 4:

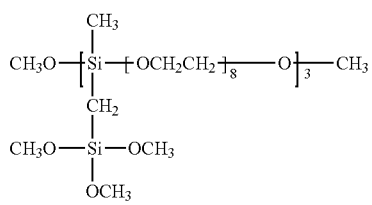

Formula 5:

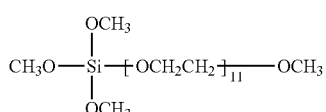

Formula 6:

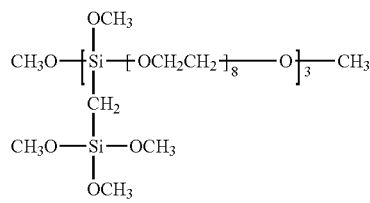

Formula 7:

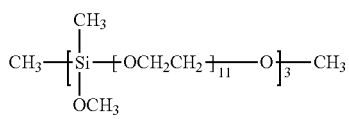

Formula 8:

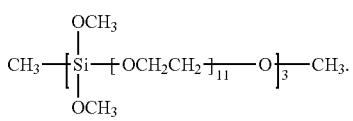

In another embodiment of the present invention, an organic electrolyte solution includes a silane compound which includes an end including an alkoxy group directly connected to a silicon atom, and another end including a polar repeating unit connected to the silicon atom.

Functions of the silane compound in the organic electrolyte solution will now be described. However, these functions are exemplary only and are not intended to limit the scope of the invention.

The alkoxy group directly connected to the silicon atom in the silane compound reacts with a hydroxyl group, etc. present on the surface of the metal active material. Thus, the silane compound is chemically adsorbed onto the surface of the metal active material by a covalent bond. For example, the silane compound and the metal active material may form a M—O—Si—R linkage where M is the metal active material and R is a substituent. That is, through the chemical adsorption, the silane compound forms a monolayer on the surface of the active material. The monolayer of the silane compound can prevent direct contact between the active material and the electrolyte, and furthermore, can prevent crack formation, which may result from volumetric changes in the anode active material during lithium intercalation/deintercalation.

The polar repeating unit on an end of the silane compound has an affinity for a polar solvent, thereby facilitating diffusion of the electrolyte and lithium ions in the electrolyte solution, together with the solvent, into the silane compound monolayer. As such, although the monolayer (a kind of a passivation layer) made of the silane compound is present on the surface of the active material, the charge/discharge rate of lithium is not significantly affected due to the easy diffusion of lithium ions into the monolayer.

Specifically, according to one embodiment of the present invention, the organic electrolyte solution includes an organic solvent having a high dielectric constant solvent and a low boiling point solvent, and a silane compound represented by Formula 1 below.

Formula 1:

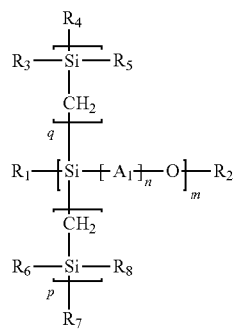

In Formula 1, n is a real number ranging from 1 to 20, m is an integer ranging from 1 to 10, and each of p and q is independently selected from 0 or 1. Each of $R_1$, $R_3$, $R_4$, $R_5$, $R_6$, $R_7$, and $R_8$ is independently selected from unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups. $R_2$ is selected from unsubstituted $C_{1-20}$ alkyl groups and halogen substituted $C_{1-20}$ alkyl groups. $A_1$ is a polar repeating unit selected from $C_{1-5}$ oxyalkylene groups, carbonyl groups,

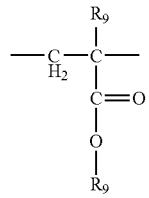

groups and mixtures thereof. In the $A_1$ repeating unit, $R_9$ is selected from hydrogen, unsubstituted $C_{1-20}$ alkyl groups and halogen substituted $C_{1-20}$ alkyl groups. At least one of $R_3$, $R_4$, $R_5$, $R_6$, $R_7$, and $R_8$ is selected from unsubstituted $C_{1-20}$ alkoxy groups and halogen substituted $C_{1-20}$ alkoxy groups.

According to another embodiment, the silane compound of Formula 1 above is a compound represented by Formula 2 below.

Formula 2:

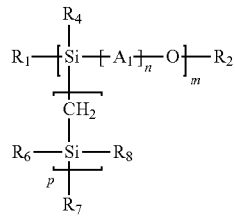

In Formula 2, $R_1$, $R_2$, $R_4$, $R_6$, $R_7$, $R_8$, n, m, and p are as defined above with respect to Formula 1.

According to one embodiment, In the silane compound of Formula 1 or 2, $A_1$ may be selected from oxyethylene groups, oxypropylene groups, oxybutylene groups, and the like. According to another embodiment, at least one of $R_4$, $R_6$, $R_7$, and $R_8$ may be selected from methoxy groups, ethoxy groups, propoxy groups, butoxy groups, pentoxy groups, and the like.

In another embodiment, the silane compound in the organic electrolyte solution is selected from compounds represented by Formulae 3 through 8 below and combinations thereof.

Formula 3:

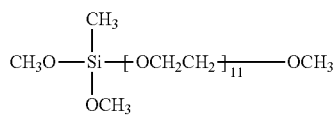

Formula 4:

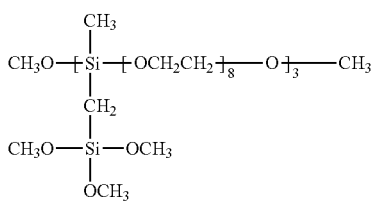

Formula 5:

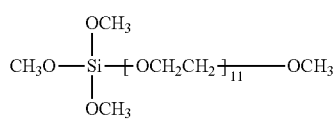

Formula 6:

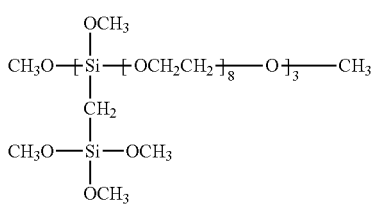

Formula 7:

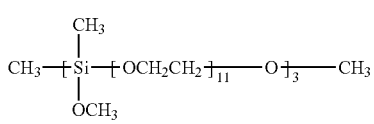

Formula 8:

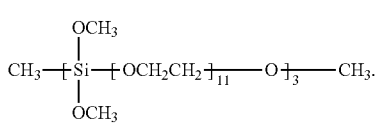

In one embodiment of the organic electrolyte solution, the silane compound may be present in an amount ranging from about 0.5 to about 20 wt % based on the total weight of the organic solvent. In another embodiment, the silane compound is present in an amount ranging from about 1 to about 15 wt % based on the total weight of the organic solvent. If the silane compound is present in an amount exceeding about 20 wt %, charge/discharge characteristics may be adversely affected due to a shortage of effective material influencing the performance of the battery. On the other hand, if the silane compound is present in an amount less than about 0.5 wt %, it may be difficult to sufficiently achieve the desired effect.

The high dielectric constant solvent is not particularly limited and can be any such solvent commonly used in the art. For example, in one embodiment, the high dielectric constant solvent may be selected from cyclic carbonates (e.g., ethylene carbonate, propylene carbonate, and butylene carbonate) and gamma-butyrolactone.

Similarly, the low boiling point solvent is not limited and may be any such solvent commonly used in the art. For example, in one embodiment, the low boiling point solvent may be selected from chain carbonates (e.g., dimethyl carbonate, ethylmethyl carbonate, diethyl carbonate, and dipropyl carbonate), dimethoxyethane, diethoxyethane, fatty acid ester derivatives, and the like.

In one embodiment, the high dielectric constant solvent and the low boiling point solvent are mixed in a ratio ranging from about 1:1 to about 1:9 by volume. If the mixture ratio of the high dielectric constant solvent and the low boiling point solvent is outside this range, discharge capacity and charge/discharge cycle life may be reduced.

The lithium salt is also not limited and may be any lithium salt commonly used in lithium batteries. For example, in one embodiment, the lithium salt may be selected from $LiClO_4$, $LiCF_3SO_3$, $LiPF_6$, $LiN(CF_3SO_2)_2$, $LiBF_4$, $LiC(CF_3SO_2)_3$, $LiN(C_2F_5SO_2)_2$ and combinations thereof.

In one embodiment, the concentration of the lithium salt in the organic electrolyte solution may range from about 0.5 to about 2M. If the concentration of the lithium salt is less than about 0.5M, the conductivity of the organic electrolyte solution may be reduced, thereby degrading the performance of the organic electrolyte solution. On the other hand, if the concentration of the lithium salt exceeds about 2.0M, the viscosity of the organic electrolyte solution may increase, thereby decreasing the mobility of lithium ions.

In one embodiment, the organic electrolyte solution of the present invention includes $LiPF_6$ as the lithium salt, ethylene carbonate as the high dielectric constant solvent, diethyl carbonate as the low boiling point solvent, and poly(ethyleneglycol)dimethoxy methyl silane (n=11) or poly(trimethoxy silyl methyl octaethyleneglycol methyl methoxy silane)dimethylether (n=3, m=8) as the silane compound.

In one embodiment of the present invention, the $C_{1-20}$ alkoxy group used in the silane compound includes a straight or branched radical. In one embodiment, the radical includes a straight or branched radical having from 1-12 carbon atoms. In another embodiment, the alkoxy radical is a lower alkoxy having from 1-6 carbon atoms. Nonlimiting examples of suitable alkoxy radicals include methoxy radicals, ethoxy radicals, n-propoxy radicals, isopropoxy radicals, n-butoxy radicals, isobutoxy radicals, sec-butoxy radicals, t-butoxy radicals, pentoxy radicals, and hexoxy radicals. In yet another embodiment, the radical includes a lower alkoxy radical having from 1-3 carbon atoms.

In another embodiment of the present invention, the $C_{1-20}$ alkyl group used in the silane compound includes a straight or branched radical. In one embodiment, the radical is a straight or branched radical having from 1-12 carbon atoms. In another embodiment, the alkyl radical is a lower alkyl having from 1-6 carbon atoms. Nonlimiting examples of suitable alkyl radicals include methyl radicals, ethyl radicals, n-propyl radicals, isopropyl radicals, n-butyl radicals, isobutyl radicals, sec-butyl radicals, t-butyl radicals, pentyl radicals, iso-amyl radicals, and hexyl radicals. In yet another embodiment, the alkyl radical is a lower alkyl radical having from 1-3 carbon atoms.

In one embodiment, the $C_{6-30}$ aryl group used in the silane compound may be a single aryl group or a combination of aryl groups. The aryl group includes a carbocyclic aromatic system having from 6-30 carbon atoms and containing one or more rings. The rings may be attached to each other as a pendant group or may be fused. The term "aryl," as used herein, means an aromatic radical, nonlimiting examples of which include phenyl radicals, naphthyl radicals, tetrahydronaphthyl radicals, indenyl radicals, and biphenyl radicals. In one embodiment, the aryl group is a phenyl group. In another embodiment, the aryl group may have from 1-3 substituent groups selected from hydroxy groups, halo groups, haloalkyl groups, nitro groups, cyano groups, alkoxy groups, and lower alkylamino groups.

In one embodiment, the $C_{2-30}$ heteroaryl group used in the silane compound is a 5-30 member, monovalent, monocyclic or bicyclic aromatic radical containing from 1-3 hetero atoms selected from N, O, P, and S. The term "heteroaryl," as used herein, refers to monovalent, monocyclic or bicyclic aromatic radicals in which a heteroatom in a ring is oxidized or quaternized to form, for example, an N-oxide or a quaternary salt. Nonlimiting examples of suitable heteroaryl groups include thienyl groups, benzothienyl groups, pyridyl groups, pyrazinyl groups, pyrimidinyl groups, pyridazinyl groups, quinolinyl groups, quinoxalinyl groups, imidazolyl groups, furanyl groups, benzofuranyl groups, thiazolyl groups, isoxazolyl groups, benzisoxazolyl groups, benzimidazolyl groups, triazolyl groups, pyrazolyl groups, pyrrolyl groups, indolyl groups, 2-pyridonyl groups, 4-pyridonyl groups, N-alkyl-2-pyridonyl groups, pyrazinonyl groups, pyridazinonyl groups, pyrimidinonyl groups, oxazolonyl groups, N-oxides thereof (e.g., pyridyl N-oxide, quinolinyl N-oxide), and quaternary salts thereof.

Figure 4:
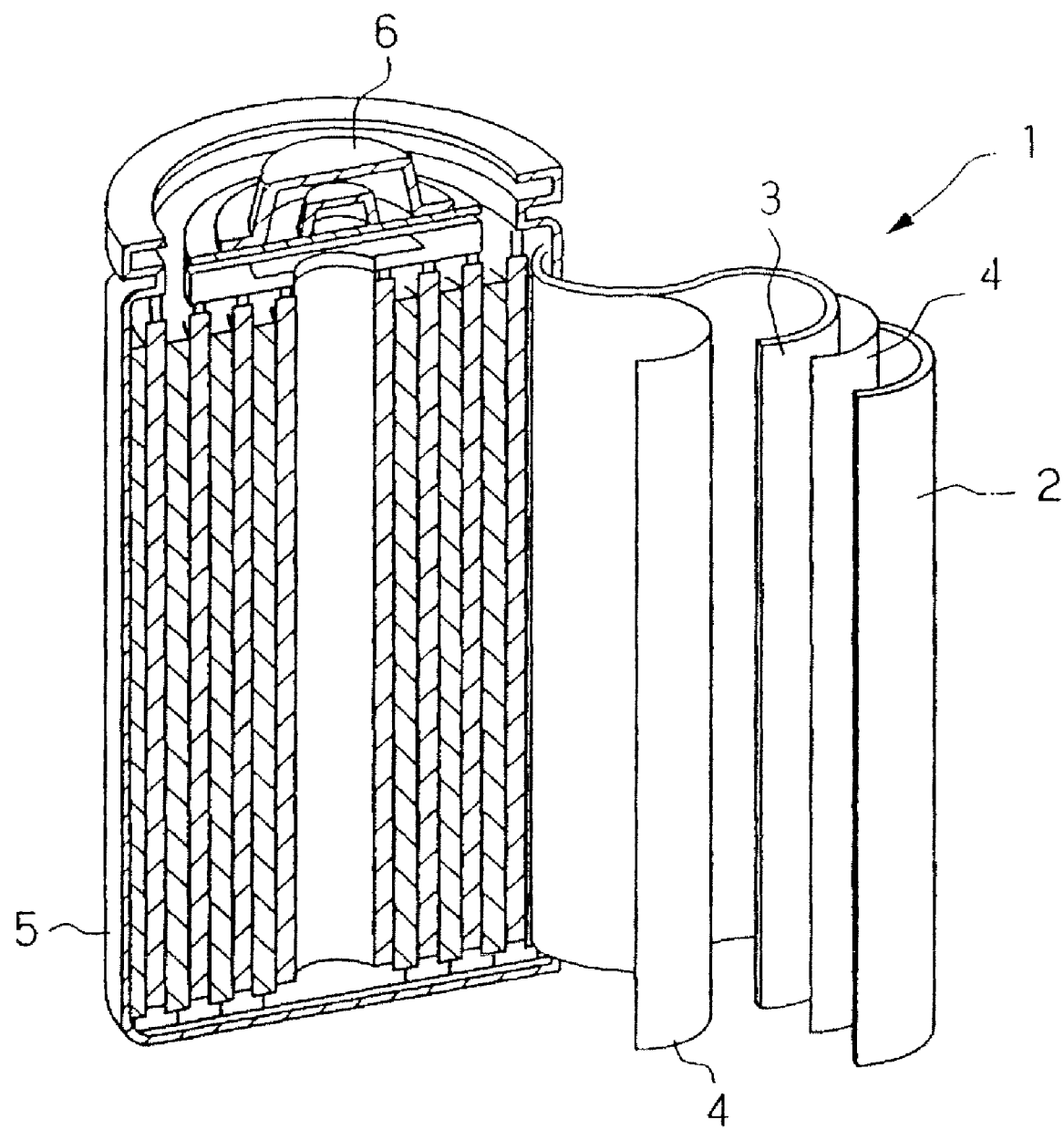
FIG. 4 is a schematic perspective view of a lithium battery according to one embodiment of the present invention.

According to another embodiment, as shown in FIG. 4, a lithium battery 1 includes an electrode assembly comprising a cathode 2, an anode 3, and a separator 4 positioned between the cathode 2 and anode 3. The electrode assembly is wound and placed in a battery case 5 and sealed with a cap assembly 6 to form a lithium battery. An organic electrolyte solution including an above-described silane compound according to one embodiment of the present invention is injected into the battery case to complete the lithium battery. The shape of the lithium battery is not particularly limited. Furthermore, the lithium battery may be a lithium primary battery as well as a lithium secondary battery. For example, the battery may be a lithium ion battery, a lithium ion polymer battery, or a lithium sulfur battery.

According to one embodiment of the present invention, the lithium battery can be manufactured as follows.

First, a cathode active material, a conducting agent, a binder, and a solvent are mixed to prepare a cathode active material composition. The cathode active material composition is directly coated on an aluminum current collector and dried to prepare a cathode plate. Alternatively, a cathode plate may also be prepared by casting the cathode active material composition on a separate support to form a film, separating the film from the support and laminating the film on an aluminum current collector.

The cathode active material is not limited and can be any lithium-containing metal oxide commonly used in the art. Nonlimiting examples of suitable cathode active materials include $LiCoO_2$, $LiMn_xO_{2x}$, $LiNi_{x-1}Mn_xO_{2x}$ (where x is 1 or 2), $Ni_{1-x-y}Co_xMn_yO_2$ ($0 \leq x \leq 0.5$, $0 \leq y \leq 0.5$), and the like.

One nonlimiting example of a suitable conducting agent is carbon black.

Nonlimiting examples of suitable binders include vinylidene fluoride/hexafluoropropylene copolymers, polyvinylidenefluoride (PVdF), polyacrylonitrile, polymethylmethacrylate, polytetrafluoroethylene, and mixtures thereof. Other nonlimiting examples of suitable binders include styrene butadiene rubber-based polymers.

Nonlimiting examples of suitable solvents include N-methylpyrrolidone (NMP), acetone, water, and the like. The cathode active material, the conducting agent, the binder, and the solvent are each used in an amount commonly used in lithium batteries.

Similarly, an anode active material, a conducting agent, a binder, and a solvent are mixed to prepare an anode active material composition. The anode active material composition is directly coated on a copper current collector to form an anode plate. Alternatively, the anode active material composition is cast on a separate support to form a film which is then removed from the support and laminated on a copper current collector to obtain an anode plate. The anode active material, the conducting agent, the binder, and the solvent are each used in an amount commonly used in lithium batteries.

Nonlimiting examples of suitable anode active materials include silicon metal, silicon thin films, lithium metal, lithium alloys, carbonaceous materials, and graphite.

The conducting agent, the binder, and the solvent in the anode active material composition are the same as those in the cathode active material composition. In some embodiments, the cathode active material composition and the anode active material composition may further include a plasticizer to form pores inside the electrode plates.

Any separator commonly used in lithium batteries may be used. For example, a separator having low resistance against ion mobility of the electrolyte and good impregnation with the electrolyte solution can be used. Nonlimiting examples of suitable separators include woven or nonwoven fabrics of glass fibers, polyester, Teflon, polyethylene, polypropylene, polytetrafluoroethylene (PTFE), and combinations thereof. In one embodiment, a windable separator made of a material such as polyethylene or polypropylene may be used in lithium ion batteries, and a separator having good impregnation with the organic electrolyte solution may be used in lithium ion polymer batteries.

According to one embodiment, the separator can be manufactured as follows.

A polymer resin, a filler, and a solvent are mixed to prepare a separator composition. The separator composition is directly coated on an electrode and dried to form a separator film. Alternatively, the separator composition is cast on a separate support and dried to form a film, which is then separated from the support and laminated on an electrode.

The polymer resin is not particularly limited, and may be selected from any binder materials used in electrode plates. Nonlimiting examples of suitable polymer resins include vinylidenefluoride/hexafluoropropylene copolymers, polyvinylidenefluoride, polyacrylonitrile, polymethylmethacrylate, and mixtures thereof. In one embodiment, the polymer resin comprises a vinylidenefluoride/hexafluoropropylene copolymer containing from about 8 to about 25 wt % of hexafluoropropylene.

The separator is disposed between the cathode plate and the anode plate to form a battery structure. The battery structure is wound or folded and encased in a cylindrical or square battery case, and an organic electrolyte solution according to an embodiment of the present invention is then injected into the case to complete a lithium ion battery.

Alternatively, battery structures are stacked to form a bicell structure and impregnated with an organic electrolyte solution according to an embodiment of the present invention. The resultant structure is received in a pouch and sealed to complete a lithium ion polymer battery.

The present invention will now be described with reference to the following examples. These examples are provided for illustrative purposes only and are not intended to limit the scope of the invention.

EXAMPLE 1

Preparation of Silane Compound of Formula 3

5.5 g of poly(ethyleneglycol)methyl ether (Mn=550) was dried in a 60° C. vacuum oven for 12 hours to remove moisture. Then, the dried compound was diluted with 60 Ml of tetrahydrofuran, and 0.012 mol of triethylamine was added. The mixed solution was cooled to 0° C., and 0.01 mol of chlorodimethoxymethylsilane was gradually added. Then, the reaction mixture was gradually heated to room temperature and allowed to stand for 15 hours. After the reaction was terminated, the resultant solution was filtered through a CELITE® filtering medium. The filtrate was subjected to reduced pressure of 0.1 torr to remove volatile materials, and concentrated to give a silane compound represented by Formula 3 above.

EXAMPLE 2

Preparation of Silane Compound of Formula 4

0.03 mol of vinyltrimethoxysilane, 0.1 Ml of platinum(0)-1,3-divinyl-1,1,3,3-tetramethyldisiloxane complex solution in xylene, and 50 Ml of tetrahydrofuran were placed in a flask. The flask was cooled to 0° C., and 0.033 mol of dichloromethylsilane was gradually added to the flask. The flask was gradually heated to room temperature and incubated for 20 hours. The reaction solution was incubated under reduced pressure of 0.1 torr to remove volatile materials, and concentrated. 100 ml of hexane and 5 g of activated carbon were added to the concentrate, and the reaction mixture was stirred for one hour and filtered through a CELITE® filtering medium. The filtrate was incubated under reduced pressure of 0.1 torr to remove hexane. thereby obtaining an intermediate product.

After drying 4 g of poly(ethyleneglycol) (Mn=400) as in Example 1, a silane compound represented by Formula 4 above was prepared in the same manner as in Example 1 except that 2.63 g of the intermediate product was used instead of the chlorodimethoxymethylsilane.

EXAMPLE 3

Preparation of Electrolyte Solution

An organic electrolyte solution was prepared by adding 5 wt % of poly(ethylene glycol) dimethyl methyl silane (n=11) of Formula 3 below as an additive to a mixed organic solvent composed of 30 vol % of ethylene carbonate and 70 vol % of diethyl carbonate, and using 1M $LiN(C_2F_5SO_2)_2$(BETI) as a lithium salt.

Formula 3:

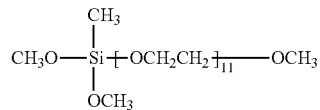

EXAMPLE 4

Preparation of Electrolyte Solution

An organic electrolyte solution was prepared in the same manner as in Example 3 except that 2 wt % of poly(trimethoxy silyl methyl octaethyleneglycol methyl methoxy silane) dimethylether (n=3, m=8) of Formula 4 below was used instead of the poly(ethyleneglycol)dimethoxy methyl silane (n=11) of Formula 3.

Formula 4:

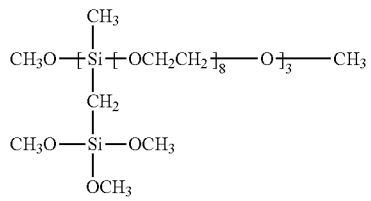

COMPARATIVE EXAMPLE 1

Preparation of Electrolyte Solution

An organic electrolyte solution was prepared using a mixed organic solvent composed of 30 vol % of ethylene carbonate and 70 vol % of diethyl carbonate and 1M $LiN(C_2F_5SO_2)_2$ (BETI) as a lithium salt in the absence of an additive.

COMPARATIVE EXAMPLE 2

Preparation of Electrolyte Solution

An organic electrolyte solution was prepared in the same manner as in Example 3 except that vinyl triethoxy silane of Formula 12 below was used instead of the poly(ethyleneglycol)dimethoxy methyl silane (n=11) of Formula 3.

Formula 12:

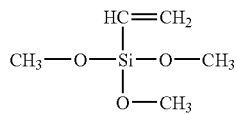

EXAMPLE 5

Manufacture of Lithium Ion Battery 6 wt % of silicon powder having an average particle size of 0.1 μm and 90 wt % of graphite powder as anode active materials, 4 wt % of PVdF as a binder, and 100 ml of NMP were well mixed and a ceramic ball was added to the mixture. The reaction components were thoroughly stirred for about 10 hours and the resultant mixture was cast on copper foil having a thickness of 19 μm using a doctor blade with a 300 μm gap to obtain anodes. The anodes were placed in a 90° C. oven and dried for about 10 hours to evaporate the NMP. Then, the anodes were roll-pressed to complete anodes having a thickness of 120 μm.

95 wt % of lithium cobalt oxide ($LiCoO_2$) powder having an average particle size of 20 μm and 3 wt % of amorphous carbon powder as cathode active materials, 2 wt % of PVdF as a binder, and 100 ml of NMP were thoroughly mixed. The resultant mixture was cast on aluminum foil having a thickness of 15 μm using a doctor blade with a 300 μm gap to obtain cathodes. The cathodes were placed in a 120° C. oven and dried for about 10 hours to evaporate the NMP. Then, the cathodes were roll-pressed to complete cathodes having a thickness of 120 μm.

A 2016 coin cell was manufactured using the above cathode having a diameter of 1 cm, the above anode having a diameter of 1.2 cm, a polyethylene separator, and the organic electrolyte solution prepared according to Example 3.

EXAMPLE 6

Manufacture of Lithium Ion Battery

A 2016 coin cell was prepared as in Example 5, except that the organic electrolyte solution prepared according to Example 4 was used.

COMPARATIVE EXAMPLE 3

Manufacture of Lithium Ion Battery

A 2016 coin cell was manufactured as in Example 5, except that the organic electrolyte solution prepared in Comparative Example 1 was used.

COMPARATIVE EXAMPLE 4

Manufacture of Lithium Ion Battery

A 2016 coin cell was manufactured as in Example 5, except that the organic electrolyte solution prepared in Comparative Example 2 was used.

EXPERIMENTAL EXAMPLE 1

Charge/Discharge Characteristics Test of Batteries

Prior to performing charge/discharge characteristics tests for the coin cells manufactured in Examples 5-6 and Comparative Examples 3-4, the coin cells were activated as follows. A constant-current charge was performed using 36 mA of current per 1 g of anode active material until the cell voltage reached 4.2 V. Then, the cells were charged at a constant voltage of 4.2V until the current was reduced to 9 mA per 1 g of the anode active material. Then, a constant-current discharge was performed using 36 mA of current per 1 g of the anode active material until the voltage reached 3.0V. The charge and discharge were repeated twice. Cycle life tests for the sufficiently activated coin cells were performed under the following conditions.

A constant-current charge was performed using 90 mA of current per 1 g of the anode active material until the cell voltage reached 4.2 V, and then, the cells were charged at a constant voltage of 4.2V until the current was reduced to 9 mA per 1 g of the anode active material. Then, a constant-current discharge was performed using 90 mA of current per 1 g of the anode active material until the voltage reached 3.0V to thereby obtain charge/discharge capacities. Charge/discharge efficiencies and capacity retention ratios were calculated using the charge/discharge capacities. The charge/discharge efficiencies were calculated using Equation 1 below, and the capacity retention ratios were calculated using Equation 2 below.

Charge/discharge efficiency (%)=discharge capacity/charge capacity    Equation 1:

Capacity retention ratio (%)=discharge capacity at $100^{th}$ cycle/discharge capacity at $1^{st}$ cycle    Equation 2:

The charge/discharge capacities, the charge/discharge efficiencies, and the capacity retention ratios were measured according to the number of cycles. The experimental results are summarized in Table 1 below and in FIG. 1.

TABLE 1

|  | 1st cycle | | | 100th cycle | | | |
| --- | --- | --- | --- | --- | --- | --- | --- |
|  | Charge capacity (mAh/g) | Discharge capacity (mAh/g) | Charge/discharge efficiency (%) | Charge capacity (mAh/g) | Discharge capacity (mAh/g) | Charge/discharge efficiency (%) | Capacity retention ratio (%) |
| Example 5 | 408.6 | 384.0 | 93.98 | 277.7 | 275.6 | 99.22 | 71.7 |
| Example 6 | 357.9 | 353.6 | 98.80 | 263.8 | 263.7 | 99.97 | 74.5 |
| Comparative Example 3 | 411.8 | 387.3 | 94.03 | 203.3 | 200.9 | 98.82 | 51.8 |
| Comparative Example 4 | 376.3 | 371.5 | 98.74 | 244.3 | 243.7 | 99.74 | 65.6 |

Referring to FIG. 1, the charge/discharge efficiencies at the $1^{st}$ and the $100^{th}$ cycles of the coin cells manufactured in Examples 5 and 6 were similar to those of the coin cells manufactured in Comparative Examples 3 and 4. However, the capacity retention ratios after the $100^{th}$ cycle of the coin cells manufactured in Examples 5 and 6 were 20% or more greater than those of the coin cells manufactured in Comparative Example 3 (with no additive), and about 6-10% greater than those of the coin cells manufactured in Comparative Example 4 (using an alkoxy silane compound having a functional group with no affinity to a polar solvent). These results show that silane compounds according to some embodiments of the present invention effectively prevent crack formation and agglomeration of silicon particles that occur due to volumetric changes in the metal active material during charging/discharging. In addition, silane compounds according to some embodiments of the present invention induce reversible intercalation/deintercalation of lithium ions, thereby enhancing battery cycle life.

EXPERIMENTAL EXAMPLE 2

Evaluation of Surface Morphologies of Batteries

The coin cells of Example 5 and Comparative Example 3 (after being subjected to the charge/discharge characteristics tests of Experimental Example 1) were disassembled, and surface morphologies of the anodes were examined using a scanning electron microscope. The results are shown in FIGS. 2A and 2B (Example 5) and FIGS. 3A and 3B (Comparative Example 3).

Figure 2A:
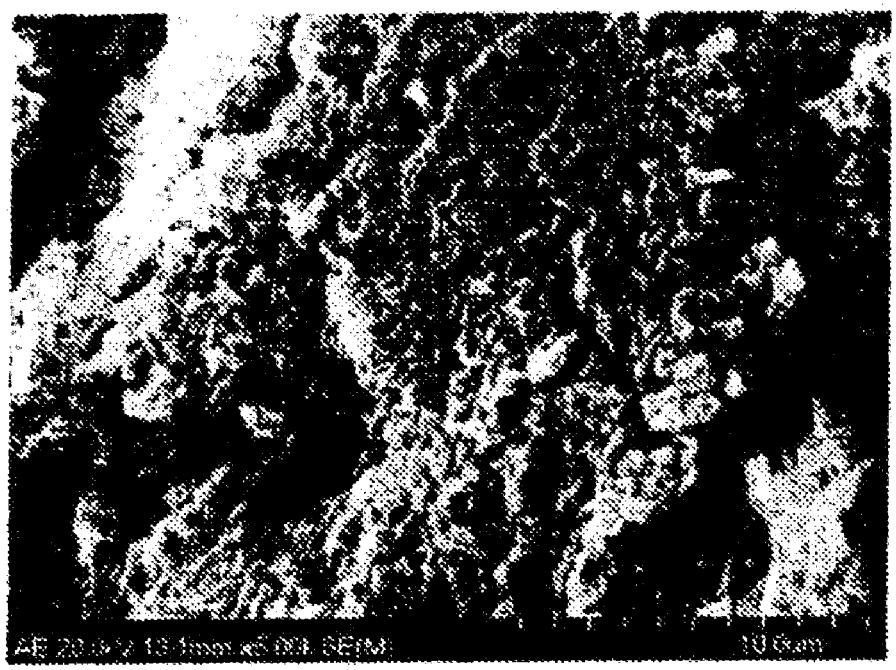
FIGS. 2A and 2B are Scanning Electron Microscope (SEM) images taken after a charge/discharge test of the surface of the anode of the lithium battery prepared according to Example 5.
Figure 2B:
Figure 3A:
FIGS. 3A and 3B are SEM images taken after a charge/discharge test of the surface of the anode of the lithium battery prepared according to Comparative Example 3.
Figure 3B:
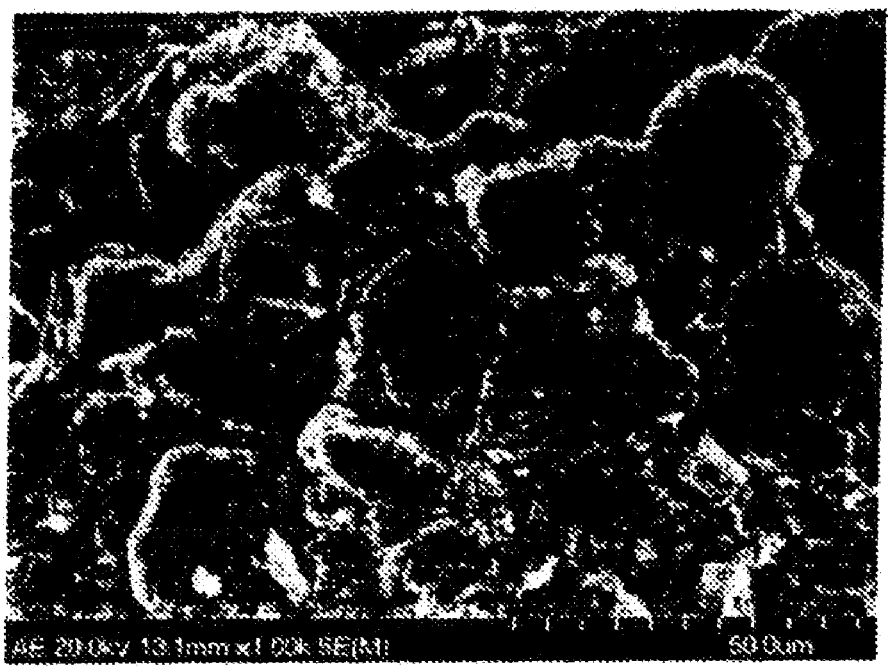

Referring to FIGS. 2A and 2B (showing the surfaces of the anodes of the coin cells of Example 5 using an organic electrolyte solution according to one embodiment of the present invention) only graphite particles were observed and no silicon particles were observed. However, referring to FIGS. 3A and 3B (showing the surfaces of the anodes of the coin cells of Comparative Example 3 using the additive-free organic electrolyte solution) silicon particles were present as agglomerates on the surfaces of the graphite particles.

These results show that the use of an organic electrolyte solution according to one embodiment of the present invention prevents agglomeration due to shrinkage and expansion of the metal active material particles during battery charging/discharging.

An electrolyte solution according to one embodiment of the present invention uses a silane compound that prevents crack formation caused by volumetric changes in the anode active material during battery charging/discharging. This improves charge/discharge characteristics, thereby improving stability, reliability, and charge/discharge efficiency of the battery. In contrast, conventional organic electrolyte solutions have higher irreversible capacities due to decomposition of the polar solvent.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. An organic electrolyte solution comprising:
a lithium salt;
an organic solvent comprising a high dielectric constant solvent and a low boiling point solvent; and
a silane compound represented by Formula 1:

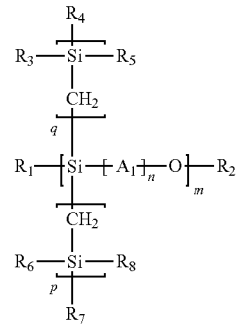

Formula 1 wherein:
n is a real number ranging from 1 to 20;
m is an integer ranging from 1 to 10;
each of p and q is independently selected from 0 or 1;
each of $R_1$, $R_3$, $R_4$, $R_5$, $R_6$, $R_7$, and $R_8$ is independently selected from the group consisting of unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups;
$R_2$ is selected from the group consisting of unsubstituted $C_{1-20}$ alkyl groups, and halogen substituted $C_{1-20}$ alkyl groups;

$A_I$ is a polar repeating unit selected from the group consisting of $C_{2-5}$ oxyalkylene groups, carbonyl groups,

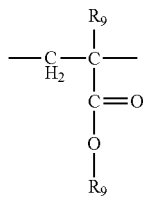

groups, and combinations thereof, wherein $R_9$ is selected from the group consisting of hydrogen, unsubstituted $C_{1-20}$ alkyl groups and halogen substituted $C_{1-20}$ alkyl groups; and at least one of $R_3$, $R_4$, $R_5$, $R_6$, $R_7$, and $R_8$ is selected from the group consisting of unsubstituted $C_{1-20}$ alkoxy groups and halogen substituted $C_{1-20}$ alkoxy groups.

2. The organic electrolyte solution of claim 1, wherein the silane compound of Formula 1 is a compound represented by Formula 2:

Formula 2

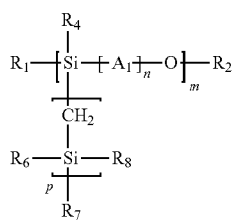

wherein:
n is a real number ranging from 1 to 20;
m is an integer ranging from 1 to 10;
p is 0 or 1;
each of $R_1$, $R_4$, $R_6$, $R_7$, and $R_8$ is independently selected from the group consisting of unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups;
$R_2$ is selected from the group consisting of unsubstituted $C_{1-20}$ alkyl groups, and halogen substituted $C_{1-20}$ alkyl groups;
$A_I$ is a polar repeating unit selected from the group consisting of $C_{2-5}$ oxyalkylene groups, carbonyl groups,

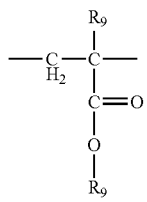

groups, and combinations thereof, wherein $R_9$ is selected from the group consisting of hydrogen, unsubstituted $C_{1-20}$ alkyl groups and halogen substituted $C_{1-20}$ alkyl groups; and at least one of $R_4$, $R_6$, $R_7$, and $R_8$ is selected from the group consisting of unsubstituted $C_{1-20}$ alkoxy groups and halogen substituted $C_{1-20}$ alkoxy groups.

3. The organic electrolyte solution of claim 1, wherein $A_I$ is an oxyalkylene group selected from the group consisting of oxyethylene groups, oxypropylene groups, oxybutylene groups, oxypentylene groups and mixtures thereof.

4. The organic electrolyte solution of claim 1, wherein at least one of $R_4$, $R_6$, $R_7$, and $R_8$ is an alkoxy group selected from the group consisting of methoxy groups, ethoxy groups, propoxy groups, butoxy groups, pentoxy groups and mixtures thereof.

5. The organic electrolyte solution of claim 1, wherein the silane compound is present in an amount ranging from about 0.5 to about 20 wt % based on the total weight of the organic solvent.

6. The organic electrolyte solution of claim 1, wherein the silane compound is present in an amount ranging from about 1 to about 15 wt % based on the total weight of the organic solvent.

7. The organic electrolyte solution of claim 1, wherein a concentration of the lithium salt ranges from about 0.5 to about 2.0 M.

8. The organic electrolyte solution of claim 1, wherein the high dielectric constant solvent is selected from the group consisting of ethylene carbonate, propylene carbonate, butylene carbonate, gamma butyrolactone and mixtures thereof.

9. The organic electrolyte solution of claim 1, wherein the low boiling point solvent is selected from the group consisting of dimethyl carbonate, ethylmethyl carbonate, diethyl carbonate, dipropyl carbonate, dimethoxyethane, diethoxyethane, fatty acid ester derivatives and mixtures thereof.

10. A lithium battery comprising:
a cathode;
an anode; and
the organic electrolyte solution of claim 1.

11. The lithium battery of claim 10, wherein the silane compound of Formula 1 is a compound represented by Formula 2:

Formula 2

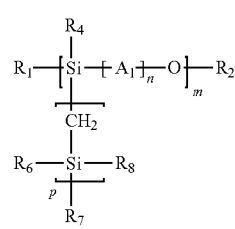

wherein:
n is a real number ranging from 1 to 20;
m is an integer ranging from 1 to 10;
p is 0 or 1;
each of $R_1$, $R_4$, $R_6$, $R_7$, and $R_8$ is independently selected from the group consisting of unsubstituted $C_{1-20}$ alkoxy groups, halogen substituted $C_{1-20}$ alkoxy groups, unsubstituted $C_{1-20}$ alkyl groups, halogen substituted $C_{1-20}$ alkyl groups, unsubstituted $C_{6-30}$ aryl groups, halogen substituted $C_{6-30}$ aryl groups, unsubstituted $C_{2-30}$ heteroaryl groups, and halogen substituted $C_{2-30}$ heteroaryl groups;

$R_2$ is selected from the group consisting of unsubstituted $C_{1-20}$ alkyl groups, and halogen substituted $C_{1-20}$ alkyl groups;

$A_l$ is a polar repeating unit selected from the group consisting of $C_{2-5}$ oxyalkylene groups, carbonyl groups,

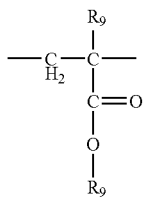

groups, and combinations thereof, wherein $R_9$ is selected from the group consisting of hydrogen, unsubstituted $C_{1-20}$ alkyl groups and halogen substituted $C_{1-20}$ alkyl groups; and at least one of $R_4$, $R_6$, $R_7$, and $R_8$ is selected from the group consisting of unsubstituted $C_{1-20}$ alkoxy groups and halogen substituted $C_{1-20}$ alkoxy groups.

12. The lithium battery of claim 10, wherein $A_1$ is an oxyalkylene group selected from the group consisting of oxyethylene groups, oxypropylene groups, oxybutylene groups, oxypentylene groups and mixtures thereof.

13. The lithium battery of claim 10, wherein at least one of $R_4$, $R_6$, $R_7$, and $R_8$ is an alkoxy group selected from the group consisting of methoxy groups, ethoxy groups, propoxy groups, butoxy groups, pentoxy groups and mixtures thereof.

14. An organic electrolyte solution comprising:
a lithium salt;
an organic solvent comprising a high dielectric constant solvent and a low boiling point solvent; and
a silane compound selected from the group consisting of compounds represented by
Formulae 3 through 8:

Formula 3
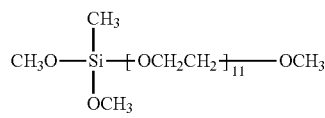

Formula 4
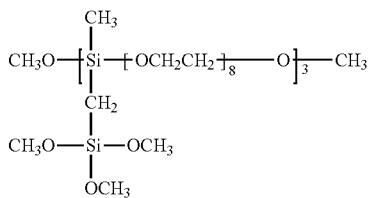

Formula 5
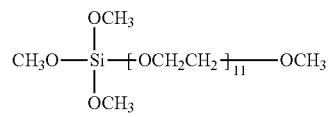

Formula 6
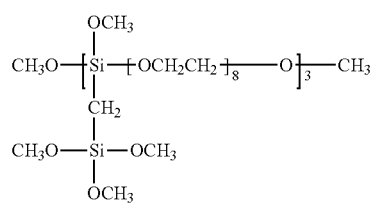

Formula 7
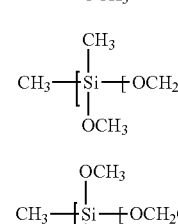

Formula 8
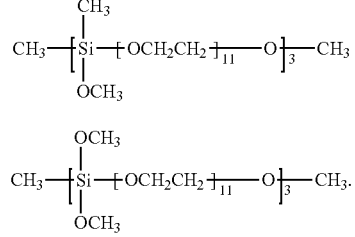

15. A lithium battery comprising:
a cathode;
an anode; and
the organic electrolyte solution of claim 14.

16. The organic electrolyte solution of claim 14, wherein the silane compound is present in an amount ranging from about 0.5 to about 20 wt % based on the total weight of the organic solvent.

17. The organic electrolyte solution of claim 14, wherein the silane compound is present in an amount ranging from about 1 to about 15 wt % based on the total weight of the organic solvent.

18. The organic electrolyte solution of claim 14, wherein a concentration of the lithium salt ranges from about 0.5 to about 2.0 M.

19. The organic electrolyte solution of claim 14, wherein the high dielectric constant solvent is selected from the group consisting of ethylene carbonate, propylene carbonate, butylene carbonate, gamma butyrolactone and mixtures thereof.

20. The organic electrolyte solution of claim 14, wherein the low boiling point solvent is selected from the group consisting of dimethyl carbonate, ethylmethyl carbonate, diethyl carbonate, dipropyl carbonate, dimethoxyethane, diethoxyethane, fatty acid ester derivatives and mixtures thereof.

* * * * *

UNITED STATES PATENT AND TRADEMARK OFFICE
CERTIFICATE OF CORRECTION

PATENT NO. : 8,034,489 B2  Page 1 of 1
APPLICATION NO. : 11/688783
DATED : October 11, 2011
INVENTOR(S) : Young-Gyoon Ryu et al.

It is certified that error appears in the above-identified patent and that said Letters Patent is hereby corrected as shown below:

In the Claims

| | |
|---|---|
| Column 19, Claim 1, line 1. | Delete "$A_l$" |
| | Insert -- $A_1$ -- |
| Column 19, Claim 2, line 52. | Delete "$A_l$" |
| | Insert -- $A_1$ -- |
| Column 20, Claim 3, line 6. | Delete "$A_l$" |
| | Insert -- $A_1$ -- |
| Column 21, Claim 11, line 4. | Delete "$A_l$" |
| | Insert -- $A_1$ -- |

Signed and Sealed this
Twenty-eighth Day of August, 2012

David J. Kappos
*Director of the United States Patent and Trademark Office*